Figure 1E:
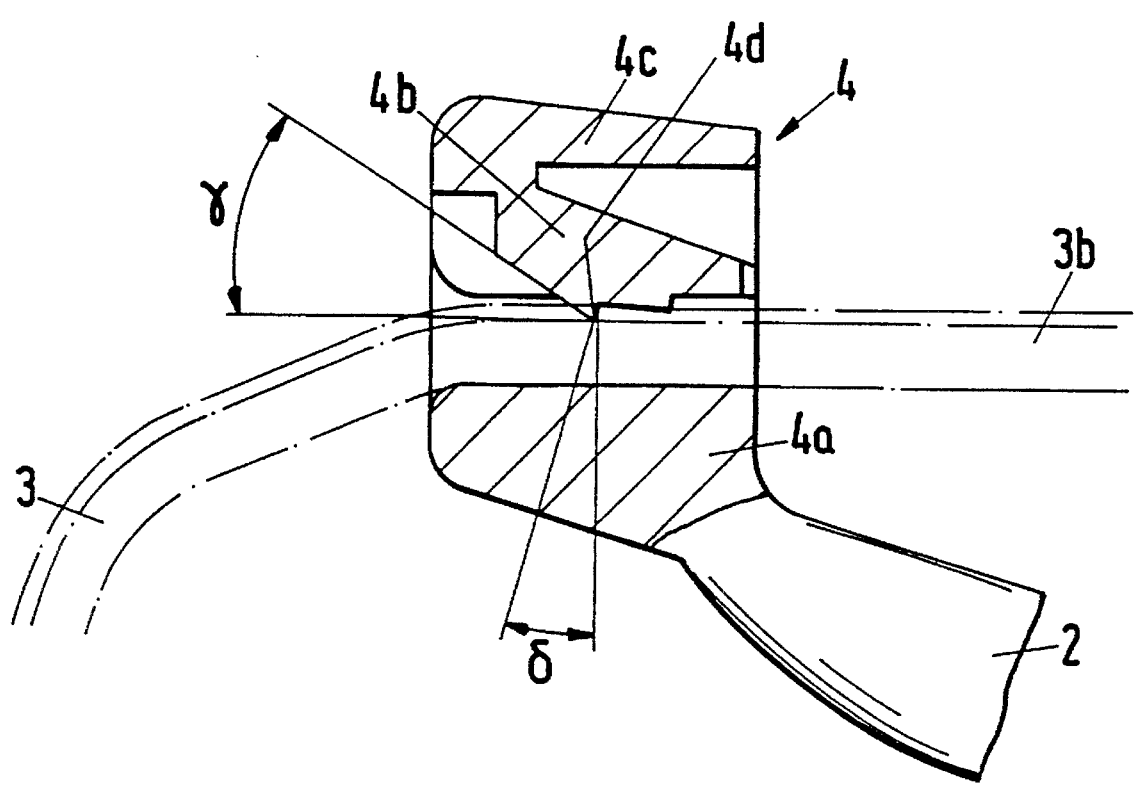

United States Patent [19]

Spotorno et al.

[11] Patent Number: 5,500,018
[45] Date of Patent: Mar. 19, 1996

[54] SEALING ELEMENT IN THE FORM OF A STRAP

[75] Inventors: Lorenzo Spotorno, Finale Ligure, Italy; Willi Fick, Wabern; Roland Willi, Neftenbach, both of Switzerland

[73] Assignees: Protek AG, Bern, Switzerland; Sulzer Medizinaltechnik AG, Winterthur, Switzerland

[21] Appl. No.: 207,776

[22] Filed: Mar. 8, 1994

[30] Foreign Application Priority Data

Mar. 23, 1993 [EP] European Pat. Off. ............ 93810207.6

[51] Int. Cl.$^6$ .................................. A61F 2/02; A61K 9/22
[52] U.S. Cl. .................. 623/11; 623/16; 623/22; 623/66; 606/74; 606/92
[58] Field of Search .................................. 623/11, 16, 18, 623/22–23, 66; 24/16 R, 16 PB, 17 R, 17 A, 17 B, 17 AP; 606/92–94, 53, 60, 72, 73, 74

[56] References Cited

U.S. PATENT DOCUMENTS

| H968 | 10/1891 | Moyles . | |
|---|---|---|---|
| 4,119,091 | 10/1978 | Partridge | 606/74 |
| 4,997,448 | 3/1991 | Filer . | |
| 5,061,287 | 10/1991 | Feiler | 606/92 |
| 5,147,366 | 9/1992 | Arroyo et al. | 606/92 |
| 5,443,483 | 8/1995 | Kirsch | 606/74 |

FOREIGN PATENT DOCUMENTS

| 0073604 | 3/1983 | European Pat. Off. . | |
|---|---|---|---|
| 0315283 | 5/1989 | European Pat. Off. . | |
| 0516569 | 12/1992 | European Pat. Off. . | |
| 2662931 | 12/1991 | France . | |
| 1430071 | 3/1976 | United Kingdom | 623/22 |
| WO90/02284 | 3/1990 | WIPO . | |

*Primary Examiner*—Randall L. Green
*Assistant Examiner*—P. Zuttarelli
*Attorney, Agent, or Firm*—Townsend and Townsend and Crew

[57] ABSTRACT

A method and apparatus for introducing a shank (5) of a prosthesis into a bone cavity is disclosed. A strap 1 having an loop portion 2 and an end portion 3 is wrapped around the shank. The end portion of the strap is then clamped by a clamping device 4 to secure the strap around the shank. The bone cavity is filled with bone cement and the lower end of the shank is introduced into the bone cavity thereby forming a gap between the shank and the outer wall of the bone cavity. A strap substantially seals this gap to minimize leakage of bone cement from the bone cavity. The clamping device 4 allows the end portion of the strap to slip relative to the clamping device when a threshold force is applied against the clamping device. In this manner, the strap will conform to the increasing cross-sectional area of the elongate body of the shank as the shank is introduced into the bone cavity.

14 Claims, 4 Drawing Sheets

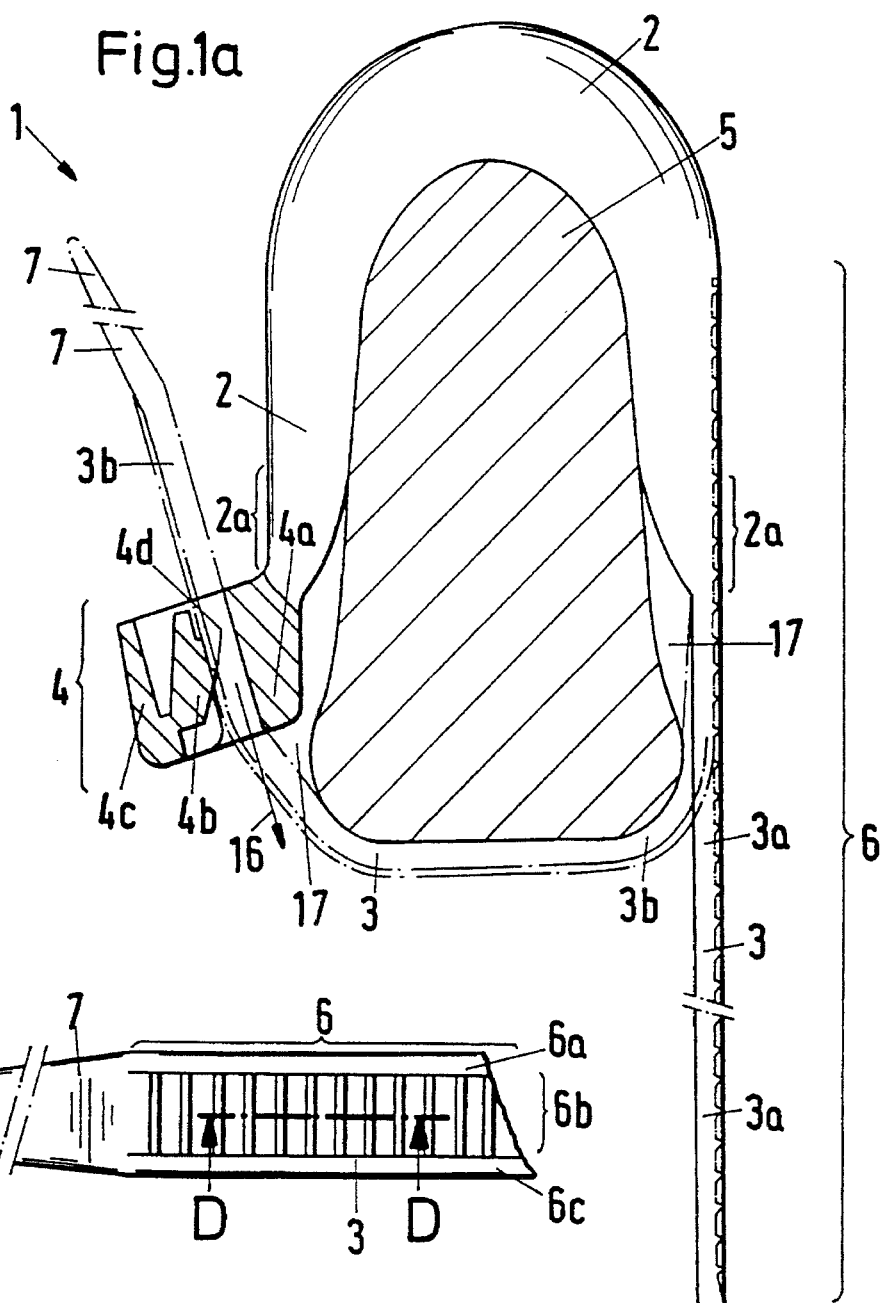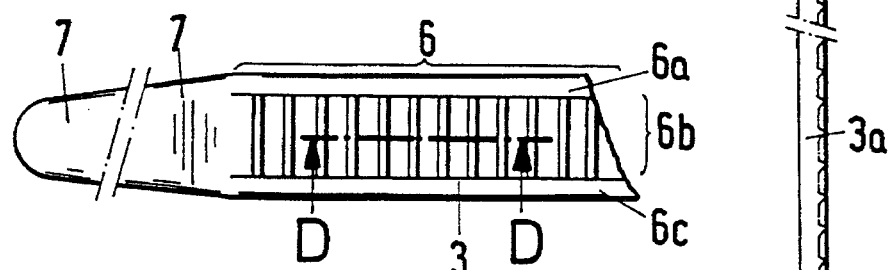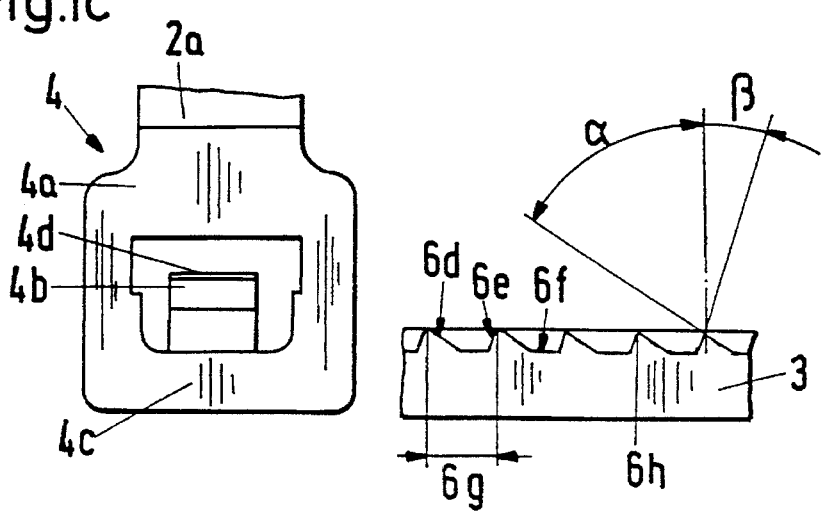

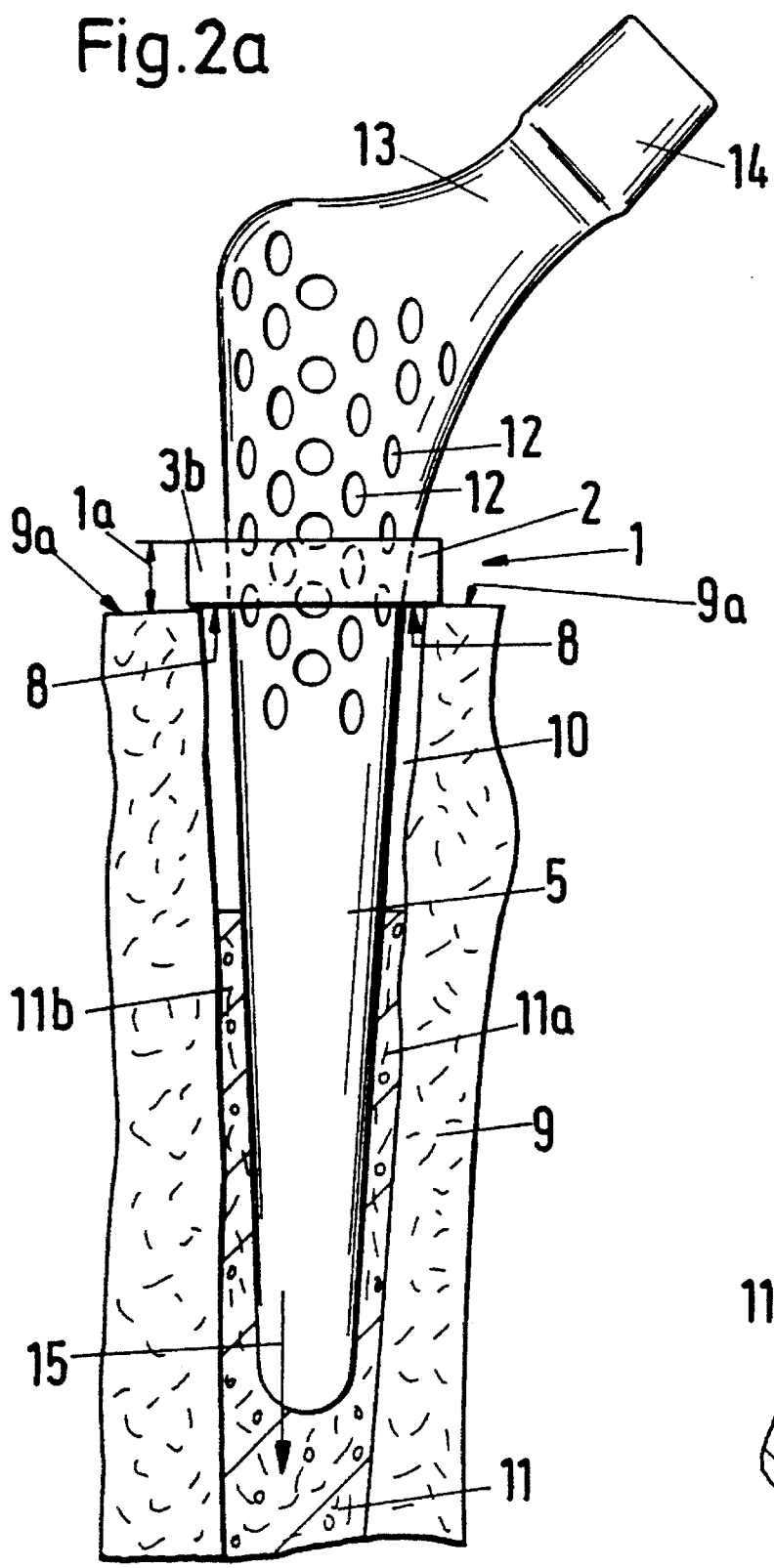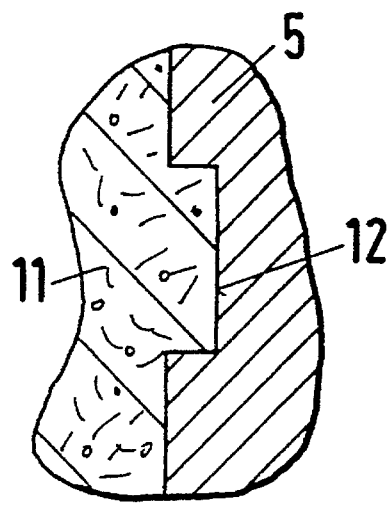

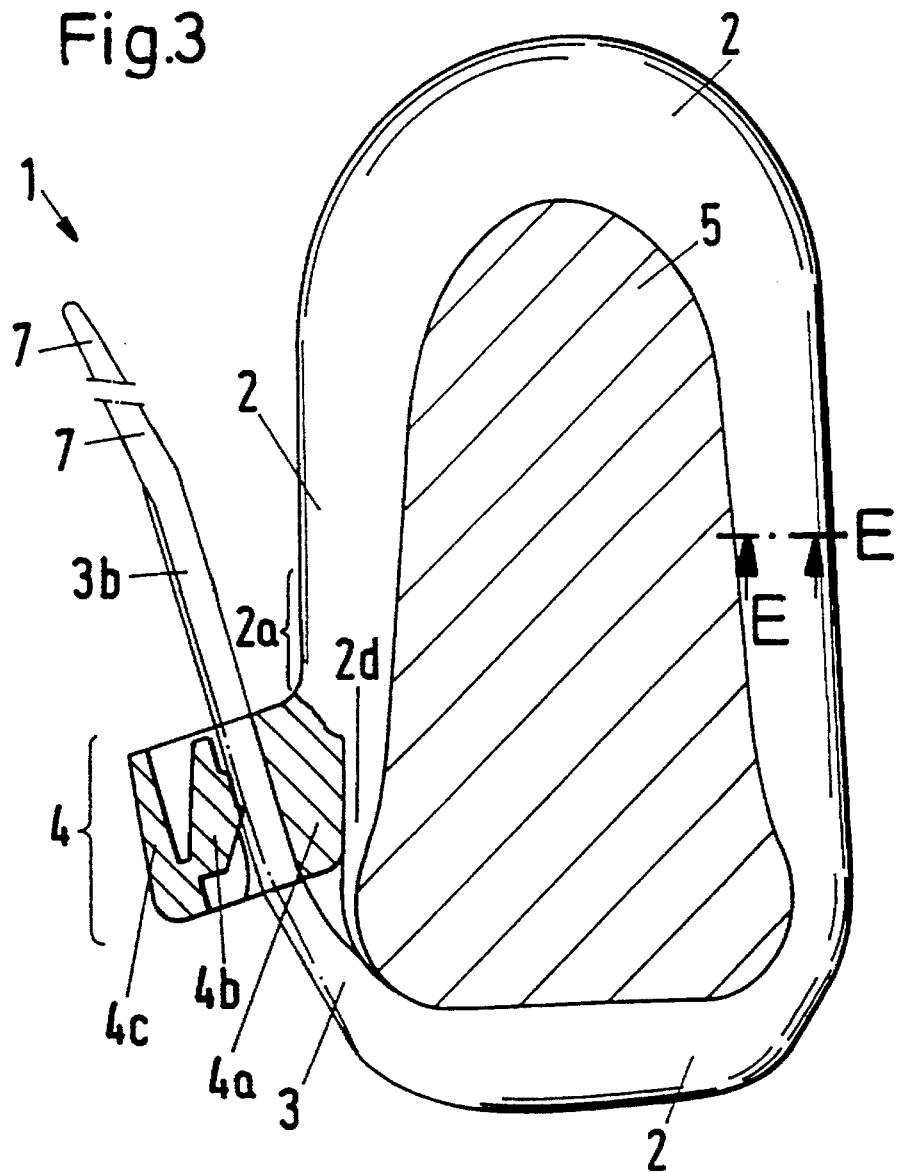
Fig.3
Fig.3a (E-E)
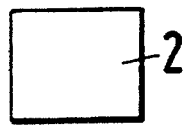
Fig.3b (E-E)
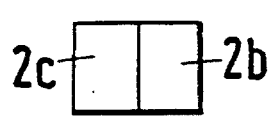
Fig.3c (E-E)
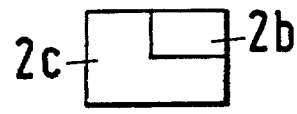

SEALING ELEMENT IN THE FORM OF A STRAP

BACKGROUND OF THE INVENTION

Prostheses, for example, hip prostheses, exhibit a shank of the prosthesis which is anchored in the bone by means of bone cement. To accomplish this a cavity is drilled in the bone and partially filled with bone cement and subsequently the shank of the prosthesis is introduced into the cavity in the bone. During the introduction of the shank, the bone cement is displaced. The cement is urged towards the opening and is forced out through the gap between the cavity in the bone and the shank of the prosthesis. The bone cement is usually obstructed against flowing out in order to keep the bone cement under a certain pressure so that the bone cement also penetrates into small pores and crevices. In order to arrive at a sealing action, the practice is known of laying a soft disc of plastics on the opening in the bone and to pierce it during the introduction of the shank of the prosthesis. This kind of sealing exhibits various disadvantages. The sealing action depends upon how the soft disc is pierced. The sealing action and hence the pressure in the bone cement is not reproducible. In addition, the introduction of the shank of the prosthesis into the cavity in the bone is obstructed, since directly before the introduction the seal has to be pierced.

SUMMARY OF THE INVENTION

The problem underlying the invention is to remove these disadvantages.

A method and apparatus for introducing a shank of a prosthesis into a bone cavity is disclosed. A strap having an loop portion and an end portion is wrapped around the shank. The end portion of the strap is then clamped by a clamping device to secure the strap around the shank. The bone cavity is filled with bone cement and the lower end of the shank is introduced into the bone cavity thereby forming a gap between the shank and the outer wall of the bone cavity. A strap substantially seals this gap to minimize leakage of bone cement from the bone cavity. The clamping device allows the end portion of the strap to slip relative to the clamping device when a threshold force is applied against the clamping device. In this manner, the strap will conform to the increasing cross-sectional area of the elongate body of the shank as the shank is introduced into the bone cavity.

The advantages of the invention are to be seen in that the sealing element exerts a reproducible sealing action predetermined by the geometrical arrangement and the sealing action may be varied within wide limits through a corresponding design of the sealing element. Through the choice of the material of the sealing element, from elastically soft material up to rigid hard material, the sealing action may be controlled. Further, the tension with which the sealing element is stretched round the shank of the prosthesis may be varied in a wide range through the clamping or closing device. In addition, openings may be provided in the sealing element for the bone cement to flow out, which makes it possible to control this leakage of cement. A further advantage is that the sealing element may be laid against the shank of the prosthesis before introducing it so that, during the introduction, the step in the treatment is omitted, of piercing a disc of plastics. A further advantage is that the sealing action may still be altered during the introduction of the shank of the prosthesis, by the tension in the sealing element being increased through pulling on the end portion.

The invention is described below with the aid of embodiments There is shown in:

FIG. 1A—A sealing element in the form of a strap which loops around the shank of the prosthesis;

FIG. 1B—An end portion of the sealing element of FIG. 1A;

FIG. 1C—A front elevation of the closing device of the sealing element;

FIG. 1D—A section (D—D) along the end portion illustrating a the set of teeth;

FIG. 1E—A section through the closing device of the sealing element;

FIG. 2A—A section through the bone of a femur with the prosthesis introduced;

FIG. 2B—A detail of a possible structure of the surface of the shank of a prosthesis;

FIG. 3—A further sealing element in the form of a strap which loops around the shank of a prosthesis;

FIGS. 3A to 3C—a section (E—E) through various embodiments of the loop portion.

FIG. 1A illustrates a sealing element 1 in the form of a strap which loops round the shank 5 of a prosthesis. The sealing element 1 in the form of a strap comprises of a clamping or closing device 4 and a loop portion 2 adjoining it, which ends in an end portion 3. The clamping or closing device 4 holds the end portion 3 under tension 16, so that the whole sealing element 1 in the form of a strap loops round the shank 5 of the prosthesis under prestress. The holding of an element in the form of a strap under prestress can naturally be solved by the most widely different embodiments. Hence the clamping or closing device 4 shown is only to be understood as one embodiment out of a plurality of possible embodiments. The clamping device 4 includes a cheek 4a, a further cheek 4c, and a springy tongue 4b which exhibits one tooth 4d acting upon the end portion 3. The end portion 3 is shown in two possible positions, as the end portion 3a in the loose state and as the end portion 3b in the fastened state in which the end portion 3b looped through the clamping device 4 is held by the latter under prestress 16. The end portion 3 ends in a tip 7 which facilitates threading the end portion 3 into the clamping device 4 between the cheek 4a and the springy tongue 4b. In the direction radially to the loop portion of the sealing element 1, is designed to be relatively wide in order to fill the gap 8 between the bone 9 and the shank 5 of the prosthesis. The end portion 3 is on the contrary made relatively narrow so that it may be introduced into the clamping device 4. Hence, a region 2a of transition results, which joins the relatively wide loop portion 2 to the narrower end portion 3, or joins the relatively wide loop portion 2 to the clamping device 4.

In the present embodiment the end portion 3 as well as the transition region 2a adjoining it exhibit on the outside a toothed region 6 which exhibits a continuous set of teeth. The sealing element 1 in the form of a strap exhibits regions 17 in which the sealing element 1 does not rest against the shank 5 of the prosthesis. Hence, for these regions 17 no sealing action results. The size of the open regions 17 may be designed to correspond with the design of the transition 2a between the loop portion 2 and the end portion 3 or respectively the clamping device 4. Naturally it is also possible to provide in the loop portion 2 open regions 17 by recesses being provided in the loop portion in such a way that between the loop portion 2 and the shank 5 of the prosthesis regions result where there is no contact.

FIG. 1B shows a plan view of an end portion 3 of a sealing element 1. The end portion 3 exhibits in the region 6 a set of teeth. The toothed region 6 exhibits along the edge on each side a border 6a, 6c which also serves for guiding the end portion 3 into the clamping device 4. Between the borders 6a, 6c at the edges there is the toothed region 6b which exhibits a continuous set of teeth. The tip 7 of the end portion 3 is again shown.

A section along D—D is shown in FIG. 1D illustrating the individual teeth 6a of the toothed regions 6. The teeth are arranged at an ordinary regular pitch 6g, the teeth exhibiting a rising flank 6e and a falling flank 6d, the angle of inclination of the toothed flanks having with respect to a direction running vertically to the end portion 3.

FIG. 1C shows a front elevation of the clamping device 4 which is connected to the region 2a of transition to the loop portion 2. The clamping device 4 exhibits a cheek 4a as well as a cheek 4c on the opposite side. On the cheek 4c is arranged a springy tongue 4b and on the tip of the latter one tooth 4d.

FIG. 1E shows a cross-section through the clamping device 4. The holding action is achieved through the interaction of the toothed region 6 on the end portion 3 with the tooth 4d on the clamping device 4. The action of the tooth 4d is determined in particular through the two angles Γ and δ of inclination of the tooth. The action of the clamping device 4 upon the end portion 3 is determined through the spring force of the tongue 4b as well as through the design of the tooth 4d and the design of the teeth 6h on the end portion 3, in particular through the mutual matching of the angles α, β, Γ and δ. The choice of the angles determines whether the connection between the clamping device 4 and the end portion 3 can, e.g., no longer be loosened or whether the connection can be loosened again. In the case of a connection which can be loosened again, the ratios between the angles influences the tension 16 which has to be exceeded in order to elongate the clamped-in part of the end portion 3. The movement of the end portion 3 in the direction of the tension 16 is effected in jerks, corresponding with the pitch 6g of the teeth. The tension which is necessary for pulling the end portion 3 out of the clamping device 4 is variable within wide limits to correspond with the ratios between the angles. Sealing elements 1 may be produced having different maximum tensions 16 which can be sustained.

FIG. 2A shows a section through a bone 9 of a femur into which a prosthesis which has a shank 5, a neck 13 and a conical peg 14 is being introduced in the direction 15 of introduction. The bone 9 has been machined in such a way that it exhibits a sufficiently large cavity 10 in the bone which has been generated in the usual way through a corresponding inner bore as well as what is usually defined as a point of section or bearing area 9a. After the drilling of the cavity 10 in the bone, a bone cement 11 is introduced into it which, during the introduction of the shank 5 of the prosthesis in the direction 15 of introduction, flows along the gap between the shank 5 of the prosthesis and the bone 9 as bone cement 11a, 11b rising towards the gap 8. Preceding the introduction of the shank 5 of the prosthesis the sealing element 1 was laid by the loop portion 2 under prestress round the shank 5 of the prosthesis and during the introduction of the shank of the prosthesis into the cavity 10 in the bone, comes to lie at some time or other upon the point of section 9a. Hence the gap 8 between the bone 9 and the shank 5 of the prosthesis becomes sealed partially or completely by the sealing element 1. Hence the rising bone cement 11a, 11b is held back by the sealing element 1 and through the pressure rising in the bone cement it fills even fine pores in the bone 9 as well, as shown in FIG. 2b, as depressions 12 in the surface of the shank 5 of the prosthesis, completely with bone cement 11. In that case, the width 1a of the sealing element 1 is preferably chosen to be such that the width 1a exceeds the dimension of a depression 12 with respect to the direction 15 of introduction. In order to avoid damage to the bone 9, the pressure built up in the bone cement 11, 11a, 11b must not come out too high. Therefore, e.g., open regions 17 are provided between the sealing element 1 and the shank 5 of the prosthesis, as shown in FIG. 1a, in order to facilitate a controlled escape of the bone cement 11. If a sealing element 1 in the form of a strap is designed in such a way that no open regions 17 result between the shank 5 of the prosthesis and the sealing element 1, through the pressure which builds up in the bone cement 11 a gap arises between the sealing element 1 and the point of section 9a, through which the bone cement 11 flows out. The resulting width of the gap between the sealing element 1 and the point of section 9a depends, inter alia, upon the tension 16 at which the end portion 3 is held by the clamping device 4. As already mentioned, the maximum tension 16 may, through the design of the teeth 6h and the design of the clamping device 4, be varied within wide limits Hence, the pressure of the bone cement 11 may also be influenced through an appropriate choice of a sealing element 1.

FIG. 3 shows a further embodiment of a sealing element 1 in the form of a strap. This embodiment exhibits no open regions 17 between the sealing element 1 and the shank 5 of the prosthesis and hence allows complete sealing between the sealing element 1 and the shank 5 of the prosthesis. In the present embodiment the loop portion 2 loops completely round the shank 5 of the prosthesis and ends only near the clamping or closing device 4 in an end portion 3 which is held under prestress by the clamping or closing device 4. For improved sealing, the loop portion 2 in the region of the clamping device 4 exhibits a lobe extension 2d which seals a possible gap between the clamping device 4 and the shank 5 of the prosthesis as well, possibly, as a gap between the end portion 3 and the shank 5 of the prosthesis. A section through the loop portion 2 along the line E—E is represented in FIGS. 3a to 3c. The sealing element 1 in the form of a strap, in particular the loop portion 2, may be built up of materials of different properties or else multilayered.

FIG. 3A shows a single-layer construction of the loop portion 2. In order to achieve good sealing properties between the loop portion 2 and the shank 5 of the prosthesis, the loop portion 2 advantageously exhibits elastic properties so that it clings everywhere to the shank 5 of the prosthesis.

FIG. 3B shows a two-layer construction of the loop portion 2. The inner loop portion 2c resting against the shank 5 of the prosthesis is in that case advantageously made elastic, whereas the outer loop portion 2b exhibits less elastic stable properties. Thus it is also possible for the loop portion 2b and the end portion 3 to be manufactured in one piece, so that the inner elastic loop portion 2c is supported by an outer less elastic loop portion 2b which is connected to the clamping device 4 and loops round the shank 5 of the prosthesis to end in the end portion 3.

FIG. 3C shows a further embodiment of a loop portion 2, in which the inner elastic loop portion 2c is made L-shaped in such a way that the elastic region rests against the shank 5 of the prosthesis as well as coming to lie against the point of section 9a on the bone 9. The outer less elastic or completely inelastic loop portion 2b guarantees the enveloping tension round the shank 5 of the prosthesis, caused by the clamping device 4.

Naturally the clamping device 4 may also be designed in such a way that the end portion 3 is connected unyieldingly to the clamping device 4. In this case the loop portion 2 and/or the end portion 3 must exhibit elastic properties so that the circumference of the stretched sealing element 1 can adapt to correspond with the increase in circumference of the shank 5 of the prosthesis.

We claim:

1. A sealing element for sealing a gap between a shank of a prosthesis and an outer wall of a bone cavity, the sealing element comprising:

a strap having an arcuate portion for circumscribing a portion of the shank and an end portion; and a clamping device adjoined to the arcuate portion of the strap, the clamping device having a coupling member cooperating with the end portion to secure the strap around the shank, the coupling member allowing the end portion to slip relative to the coupling member when a threshold force is applied against the clamping device;

whereby the strap substantially seals the gap between the shank and the outer wall of the bone cavity when the shank is inserted into the bone cavity to minimize leakage of bone cement from the bone cavity.

2. The sealing element of claim 1 wherein the coupling member is configured to allow the end portion to slip when a force against the clamping device reaches a threshold level such that the force remains substantially constant as the shank is introduced into the bone cavity.

3. The sealing element of claim 1 wherein the coupling member yields part of the length of the end portion when the threshold force is applied to the clamping device.

4. The sealing element of claim 1 wherein the arcuate portion of the strap is inelastic.

5. The sealing element of claim 1 wherein the arcuate portion of the strap is elastic.

6. The sealing element of claim 1 wherein the coupling member comprises a tongue having at least one tooth biased towards the end portion and the end portion includes a toothed region having a plurality of teeth spaced along a longitudinal direction of the strap to mate with the tooth of the tongue, the teeth of the end portion and the tooth of the tongue being shaped such that the tooth allows the end portion to slip relative to the coupling member when the threshold force is applied against the clamping device.

7. A sealing element for sealing a gap between a shank of a prosthesis and an outer wall of a bone cavity, the sealing element comprising:

a strap having an arcuate portion for circumscribing a portion of the shank and an end portion, the arcuate portion comprising a first, substantially elastic layer adjoined to a second layer that is less elastic than the first layer; and a clamping device adjoined to the arcuate portion of the strap, the clamping device having a coupling member cooperating with the end portion to secure the strap around the shank;

whereby the strap substantially seals the gap between the shank and the outer wall of the bone cavity when the shank is inserted into the bone cavity to minimize leakage of bone cement from the bone cavity.

8. The sealing element of claim 7 wherein the second layer is connected to the end portion of the strap and to the clamping device.

9. The sealing element of claim 7 wherein the end portion is fixed to the clamping device.

10. The sealing element of claim 7 wherein the the coupling member allows the end portion to slip relative to the coupling member when a threshold force is applied against the clamping device.

11. A method for introducing a shank of a prosthesis into a bone cavity, the shank having an elongate body with a generally increasing cross-sectional area from a first end to a second end, the method comprising:

wrapping an arcuate portion of a strap around a side surface of the elongate body of the shank;

fastening an end portion of the strap to the arcuate portion to secure the strap around the shank;

filling a portion of the bone cavity with bone cement;

introducing the first end of the shank into the bone cavity thereby forming a gap between the shank and an outer wall of the bone cavity;

substantially sealing the gap between the shank and the outer wall of the bone cavity with the strap to minimize leakage of bone cement from the bone cavity as the shank is introduced into the body cavity.

12. The method of claim 11 further comprising:

engaging a top wall of the bone with the strap as the shank is introducing into the bone cavity;

applying a force against the strap; and allowing the end portion of the strap to slip when the force reaches a threshold value so that the strap expands thereby allowing the strap to conform to the increasing cross-sectional area of the elongate body of the shank as the shank is introduced into the bone cavity.

13. The method of claim 11 further including the step of allowing a portion of the bone cement to egress from the bone cavity as the shank is introduced into the bone cavity.

14. The method of claim 11 wherein essentially all of the bone cement is prevented from egressing from the bone cavity as the shank is introduced into the bone cavity.

* * * * *